(12) United States Patent
Teichmann

(10) Patent No.: US 9,833,247 B2
(45) Date of Patent: Dec. 5, 2017

(54) TOOL FOR CUTTING A HELICAL GROOVE IN BONE

(71) Applicant: Gernot Teichmann, Meerbusch (DE)

(72) Inventor: Gernot Teichmann, Meerbusch (DE)

( * ) Notice: Subject to any disclaimer, the term of this patent is extended or adjusted under 35 U.S.C. 154(b) by 316 days.

(21) Appl. No.: 14/685,923

(22) Filed: Apr. 14, 2015

(65) Prior Publication Data

US 2016/0302802 A1   Oct. 20, 2016

(51) Int. Cl.
*A61B 17/16*   (2006.01)

(52) U.S. Cl.
CPC ...... *A61B 17/1631* (2013.01); *A61B 17/1624* (2013.01); *A61B 17/1655* (2013.01); *A61B 17/1673* (2013.01)

(58) Field of Classification Search
CPC ..................... A61B 17/16–17/1673
See application file for complete search history.

(56) References Cited

U.S. PATENT DOCUMENTS

2010/0233657 A1* 9/2010 Teichmann ........ A61B 17/1655
433/174
2010/0268235 A1* 10/2010 Teichmann ........ A61B 17/1655
606/80

FOREIGN PATENT DOCUMENTS

| DE | 102006057019 A | | 2/2008 | |
|---|---|---|---|---|
| DE | 102006057019 A1 | * | 2/2008 | ......... A61B 17/1673 |
| WO | WO 2008022629 A1 | * | 2/2008 | ......... A61B 17/1655 |
| WO | WO 2009056132 A2 | * | 5/2009 | ......... A61B 17/1655 |
| WO | WO 2009056132 A3 | * | 8/2009 | ......... A61B 17/1655 |

* cited by examiner

*Primary Examiner* — Zade Coley
(74) *Attorney, Agent, or Firm* — Andrew Wilford

(57) ABSTRACT

The invention relates to a surgical tool (1) for cutting a helical groove in a bone with a body (2) receiving at least a portion of a drive shaft (9) and a tool part (3) held on same comprising a functional element (5) that produces the groove in the bone by oscillating. The tool part (3) comprises a projecting, rotatable shaft (4) at whose end opposite the body (2) the pin (5) constituting the functional element extends through an aperture (8) out of the shaft (4) that, in order to remove material of the bone, can oscillate longitudinally. The shaft (4) is coupled in such a way with the drive shaft (9) that the latter exerts torque on the shaft (4) and the pin (5) at least indirectly, at least one wing (6) projecting radially from the shaft (4) that extends at a spacing beginning behind the pin (5) in the peripheral direction of the shaft (4) helically in the direction of the body (2). The drive shaft (9) has an eccentric pin (11) projecting from its front-side end that is in engagement with a vibratory shaft (7) extending through the shaft (4), the pin (5) being firmly held on the vibratory shaft (7).

10 Claims, 2 Drawing Sheets

TOOL FOR CUTTING A HELICAL GROOVE IN BONE

FIELD OF THE INVENTION

The present invention relates to a surgical tool, particularly to a tool for oral surgery for cutting a helical groove in a bone, particularly in a mandible, particularly a mandible with a body receiving at least part of a drive shaft and a tool part held thereon that comprises a functional element that produces the groove in the bone by performing an oscillating movement.

BACKGROUND OF THE INVENTION

In such a tool, the tool part comprises a projecting, rotatable shaft on whose end opposite the body a pin forming the functional element extends through an aperture out of the shaft that can be oscillated in its longitudinal direction in order to remove material of the bone, the shaft being coupled with the drive shaft such that the latter exerts a torque onto the shaft and the pin at least indirectly, and at least one wing projecting radially from the shaft that extends at a spacing beginning behind the pin in the peripheral direction of the shaft helically in the direction of the body.

To anchor dental implants in a mandible, it is necessary to provide a bore that receives the implant or an implant body holding it. Various variants of dental implants are known from the prior art. In particular, a tool of the cited type is known from German patent application DE 10 2006 057 019. However, implants in bone are necessary in surgical areas besides oral surgery.

One variant of these implants has an anchor body consisting of a massive cylindrical middle part and at least one wing projecting radially from it and extending like a screwthread around the periphery of the middle part. Two or even more such wings are also possible, the pitch of the respective wings then being substantially steeper than when only a single wing is present. The implantation of such an anchor body in the bone can be done in various ways. Something that these implantation types have in common is that a bore must first be made in the bone that receives at least the cylindrical middle part.

According to one variant, for example, the diameter of the bore can be equal to the outer diameter of the middle part, the wing or wings of the implant body then being self-cutting and the implant body being twisted into the bone like a screw, the wings cutting into the bone like the threads of a screw. However, this is only possible under the exertion of very high force or torque. In the case of a dental implant, such a screwing-in of the implant body is extremely unpleasant for the patient.

One alternative consists in designing the bore to be so large that its diameter corresponds to the overall diameter of the implant body, i.e. including the radial width of the wind. In this case, the implant body is merely pushed into the bore without the wings cutting into the bone. One drawback of this variant, however, is that a lot of bone material has to be removed and it takes a very long time until the bone material has osseointegrated to the implant body. The healing process is therefore disproportionately long.

According to a third variant, it is of course also possible to select the diameter of the bore such that it is somewhat smaller than the overall diameter of the implant body, the wing or wings does or do cut into the bone upon insertion of the implant body, but the penetration depth of the wing or wings is only minimal, for example 0.5 to 1 mm. Although the implant body is already seated firmly in the bone in this variant upon insertion, the healing process remains long, since a large volume must again be filled out with growing bone material.

OBJECT OF THE INVENTION

It is therefore the object of the present invention to provide a surgical tool for forming a groove in a bone, particularly a mandible, whose shape corresponds to the helical shape of the wing of an implant body, so that only a minimal quantity of bone material needs to be removed from the bone for the insertion of the implant body and the healing process is thus shortened substantially.

SUMMARY OF THE INVENTION

This object is achieved by a surgical tool, particularly for oral surgery, for cutting a helical groove into bone, particularly a mandible, with a body receiving at least part of a drive shaft and a tool part held onto same is proposed that comprises a functional element that produces the groove in the bone by performing an oscillating movement, the tool part comprising a projecting, rotatable shaft on whose end opposite the body a pin forming the functional element extends through an aperture out of the shaft that can be oscillated in order to remove material of the bone in its longitudinal direction. The shaft is coupled with the drive shaft such that the latter exerts a torque onto the shaft and the pin at least indirectly, at least one wing projecting radially from the shaft that extends at a spacing beginning behind the pin in the peripheral direction of the shaft helically in the direction of the body, the coupling of the shaft with the drive shaft being achieved by a hydrodynamic coupling.

One core aspect of the tool according to the invention is that the tool part performs two movements during the specified operation, namely a straight-line movement on the one hand in order to bring about the material removal on the bone, and a rotational movement on the other hand in order to drive the pin forward. Rotational movement or rotary movement of the tool, shaft or pin refers here merely to an advancement along a circular segment; that is, it does not refer to full rotations. Rather, a torque is applied to the shaft or pin that advances the pin angularly so that the tool part is worked increasingly into the bone.

Through the joint effect of the two movements, the desired groove is formed in the bone that finally extends helically into the bone. The wing projecting radially from the shaft serves to stabilize and guide the tool part.

The wing imparts a shape to the groove that corresponds substantially to the implant body to be implanted. The at least one wing enters the groove as the formation of the groove progresses, thus forming a guide for the tool or the tool part. Moreover, the wing defines the angle at which the pin is worked into the mandible, ensuring that the groove corresponds with the screwthread of the implant body to be implanted.

The extension of the wing in the radial direction corresponds at maximum to the amount by which the pin projects from the shaft so that the wing does not cause any resistance when the tool is driven into the mandible. After all, this would substantially increase the torque to be required for advancement. For this reason, the thickness of the wing is also smaller than the diameter of the pin. For example, the thickness of the wing can be between 0.5 and 1.2 mm, particularly 1 mm. The thickness of the pin is then selected so as to be commensurately larger. Since the at least one wing does not contact the outer wall of the groove and the pin precedes the wing in the direction of movement of the shaft, the wing does not actively participate in the creation of the groove. It therefore need not be embodied so as to be self-cutting and can consequently have a blunt leading edge. This offers the advantage that this edge requires no special machining.

It is sufficient for the wing to extend along ⅔ to ⅘ of the periphery of the shaft. Even if the implant to be inserted into the groove has a wing with a full or even 1.5 helical rotation around the middle part of the implant body, the wing of the tool according to the invention can also have a smaller peripheral length, because this wing only serves to stabilize and guide the tool or the pin.

The wing can have a width in the radial direction that is 0.5 to 1.1 times the diameter of the shaft. Accordingly, the pin projects from the shaft by a length that corresponds to 0.6 to 1.2 times the diameter of the shaft. For instance, if the shaft diameter is 3 mm, the overall diameter of shaft and wing can be 9 mm. Depending on the implant body to be implanted, however, a smaller or larger extension of the wing or pin in the radial direction can be implemented.

It should be noted that, before use of the surgical tool according to the invention, a bore must also be introduced into the bone whose diameter corresponds at least to the outer diameter of the shaft, preferably exactly. The tool according to the invention can then be placed onto the bone, the pin coming to rest against the bone. In order to stabilize the position, the aperture through which the pin extends can be set at a small spacing of 1 to 2 mm, for example, from the end of the shaft opposite the body, so that the shaft can be inserted with its end section reaching to the opening into the bore in the bone before the tool is put into operation. It is thus held in the bore, thereby preventing lateral movements of the tool part.

As described above, during operation of the tool according to the invention, the pin performs an oscillating movement longitudinally and, simultaneously, a rotational movement. The drive means required for this can be embodied as desired. Independent drive means can be provided, but preferably one drive effects both movements. This will be illustrated further below.

At least a portion of the surface of the pin can be diamond surfaced, for example, so that the pin acts like a file as a result of the movement, filing the bone material away. Alternatively, at least a portion of the pin can have a saw tooth profile, particularly a rotationally symmetrical saw tooth profile, so that the pin acts like a saw as a result of the movement, sawing the bone material away.

The oscillation can occur, for example, at a frequency between 25 kHz and 30 kHz, particularly at about 28 kHz, with a substantially lower frequency being possible in the case of a sawing pin, for example between 50 and 600 Hz.

In the case in which the pin acts as a file, if is sufficient for the deflection of the pin to be microscopic, i.e. 0.1 mm or less. The pin then does not operate under pressure but in contact with the mandible as needed.

The oscillation can be achieved by a vibratory drive, for example, that is coupled with a vibratory shaft extending through the shaft at the end of which the shaft is firmly held. The vibratory shaft serves to transmit vibrations from the drive to the pin, since the drive cannot be arranged in the shaft for reasons of space. However, it can be arranged in the body or outside of the tool according to the invention.

The vibratory drive can be a piezo element, for example, that produces microscopic oscillations of equal frequency upon appropriate excitation with an alternating current. The oscillations can have an amplitude of up to several 100 µm.

Alternatively, the vibratory drive can be embodied by a miniature motor or a special shaft that exerts or resists an imbalance that produces the vibrations. Rotation of the imbalance, causes the motor or the shaft to vibrate. By mechanically coupling the electric motor or the shaft to the vibratory shaft, these oscillations are transmitted to the vibratory shaft.

According to another, preferred embodiment, the oscillation can also be achieved by the drive shaft. This has the advantage that no separate vibratory drive is needed. For this purpose, the drive shaft can have an eccentric pin projecting from its front-side end that is in engagement with the vibratory shaft extending through the shaft. This engagement expediently occurs such that the eccentric pin projects into a slot that is formed in the front side of the vibratory shaft. The eccentric pin is a projection that lies off-center with respect to the axis of the drive shaft. When the shaft rotates, it consequently performs a circular movement. Through engagement of the eccentric pin in the slot, the latter acts as a catch that transmits its circular movement into a one-dimensional reciprocation of the vibratory shaft. A vibration of the vibratory shaft is thus achieved through the rotation of the drive shaft that can occur at a rate of between 20,000 and 40,000 revolutions per minute, for example.

These vibrations produced by the vibratory shaft are then transmitted from the vibratory shaft to its opposite end at which the pin is held. As a result, the pin also performs the oscillating movement.

The vibratory shaft can act not only as a transmitter of the vibration from the drive to the pin, but also as a vibration amplifier or damper. The latter can be influenced, for example, by the position of a fixed bearing that is arranged in the shaft and can be supported against the vibratory shaft. Preferably, the fixed bearing is a disk through which the vibratory shaft extends, ideally concentrically. If this fixed bearing is arranged, for example, in the middle between the site of the input or generation of the vibration and the pin, neither amplification nor damping takes place. On the other hand, if the bearing is displaced from this midpoint closer to the source of excitation, the rod or the vibratory shaft acts as an amplifier as a result of the greater spacing between fixed bearing and pin compared to the spacing between fixed bearing and excitation source, and the vibrations at the end of the vibratory shaft, i.e. in the place where the pin is held, are greater than at the beginning thereof where the vibratory drive couples the vibrations into the vibratory shaft or the eccentric pin engages in the slot.

Preferably, the position of the fixed bearing can be changed at least to a limited extend in the axial direction with respect to the vibratory shaft in order to increase or decrease the stroke of the pin depending on the desired oscillation of the pin.

Besides the way in which the oscillation of the pin is produced, its advancement, that is, the coupling of shaft and drive shaft, can be achieved in many different ways.

According to the invention, the shaft is coupled with the drive shaft via a hydrodynamic coupling, In such coupling, the transmission of force from a driving element to a driven element occurs by means of a liquid, particularly the kinetic energy of this liquid. The liquid is caused to rotate by the driving element, resulting in a vortex like a cyclone that, in turn, carries the driven element along. To move the liquid, the driving element can have fins or blades that are caused to rotate and drive the liquid. Accordingly, the driven element can also have fins or blades that are carried along by the rotating water, thus also causing the driven element to rotate.

The drive shaft having fins or blades preferably projecting radially or tangentially outward at its end lying in the body can act as a driving element, for example. Accordingly, the body having radially or tangentially inwardly oriented fins or blades on its interior can act as a driven element. These can be opposite the fin or blades of the drive shaft. Preferably, in the case of a tangential arrangement, the fins of the driving and driven element can be arranged tangential opposite each other or, in the case of blades, oppositely bent with respect to each other, so that a high level of torque is respectively transmitted to the liquid and received by it.

As a result of the hydrodynamic coupling, torque is consequently transmitted via a fluid from the drive shaft to the body. The body can have a cylindrical housing that is pivotal. The tool part can be nonrotatably fixed to the body, so that the tool part and thus also the shaft with pin are also caused to rotate by the rotation of the body or the torque is also transmitted to the tool part along with shaft and pin.

For example, the tool part can engage around the cylindrical housing like a drum and be held firmly on it, thus imparting to it the necessary stability. Accordingly, the tool part can have a tubular section for this purpose that is concentric to the body and is closed at an axial end by a perforated disk. Moreover, the shaft can be integrally formed with this section and project coaxially therefrom on the side opposite the body, so that the perforated disk closes the gap between the outside of the shaft and the inside of the tubular section.

If a vibratory shaft extends through the shaft, the shaft is commensurately tubular. For example, the shaft can be formed by a thin-walled tube. A tubular shaft offers the advantage that a liquid such as sterilized water can be conveyed through it. Ideally, the shaft has at its end facing away from the body an opening through which the liquid can emerge and rinse out the groove on the working front. Abraded bone particles are carried along and washed out of the already formed groove. The opening can be on the front end of the shaft, for example, so that the liquid flows axially toward the shaft and out of it. Alternatively or in addition, the liquid can also flow out radially through an annular gap of the aperture through which the pin extends out of the shaft. This offers the advantage that the liquid flows directly into the already created helical groove, i.e. at the working front, whereby abraded bone material that the surface structure of the pin adds is rinsed out of it and transported away. Furthermore, another opening can be present in the shaft next to the pin on the side opposite the wing on the same radial plane of the shaft as the pin through which the liquid flows.

To further improve the washing-out of abraded bone particles, the pin can be tubular and can have transverse bores in its end regions lying in the shaft through which the rinsing liquid conveyed into the shaft can enter into the pin. At the end opposite the vibratory shaft, the pin can then be open, so that the rinsing liquid can emerge in the axial direction out of this end and then flow parallel to the axis from the radial end of the groove created in the direction of the shaft. The bone chips are thus effectively rinsed out.

To prevent the shaft from resting with the full area of its front end against the bottom of the bore in the bone, the front side can be uneven. For instance, it can correspond to an arched, particularly sinusoidal line, so that the shaft rests against the bone bore only in two or more places.

According to one advantageous development of the surgical tool according to the invention, a second pin, which also extends through an aperture out of the shaft and can be oscillated in order to exert a filing effect longitudinally, can be arranged diametrically opposite from the pin. If this pin is caused to oscillate by the same source as the first pin, the second pin is moved alternately to the first pin. Through the use of two oscillating pins, a helical groove can be produced simultaneously in opposite places in the bone. This is necessary for implant bodies having wings that are offset by 180° with respect to each other like two screwthreads.

Moreover, a second wing can project from the shaft that is offset by 180° with respect to the first wing and extends helically upward at a spacing behind the second pin beginning in the peripheral direction of the shaft. In this way, a 180° symmetrical structure of the shaft is achieved. The second wing also merely serves to guide and stabilize the tool in terms of its movement as soon as the second pin has driven the formation of the corresponding groove forward so far that its trailing guide wing engages increasingly in this groove. The second wing is also shifted radially back with respect to the second pin and can thus be blunt on its periphery.

Since the surface of the pin can wear over time, it is necessary to make the pin or pins replaceable. For this purpose, the first and/or the second pin can be attached to the vibratory shaft by a screw thread. Alternatively, however, it is also possible to replace the entire tool part as a worn part. For this purpose, a provision is made that the tool part is detachably connected to, preferably plugged onto, the body.

The first and/or second pin can be round or oval in cross section, their thickness being at least as thick, preferably 10 to 20% thicker than the thickness of the wing or wings so that the wing or wings does or do not get stuck in the groove formed. Becoming stuck is possible in principle if the thickness of the pin and the thickness of the wing are substantially equal and bone chips abraded by the pin come to rest between the wings and the bone.

BRIEF DESCRIPTION OF THE DRAWING

Additional advantages and features of the invention are explained in further detail below on the basis of an illustrated embodiment and the enclosed figures.

SPECIFIC DESCRIPTION OF THE INVENTION

Figure 1:
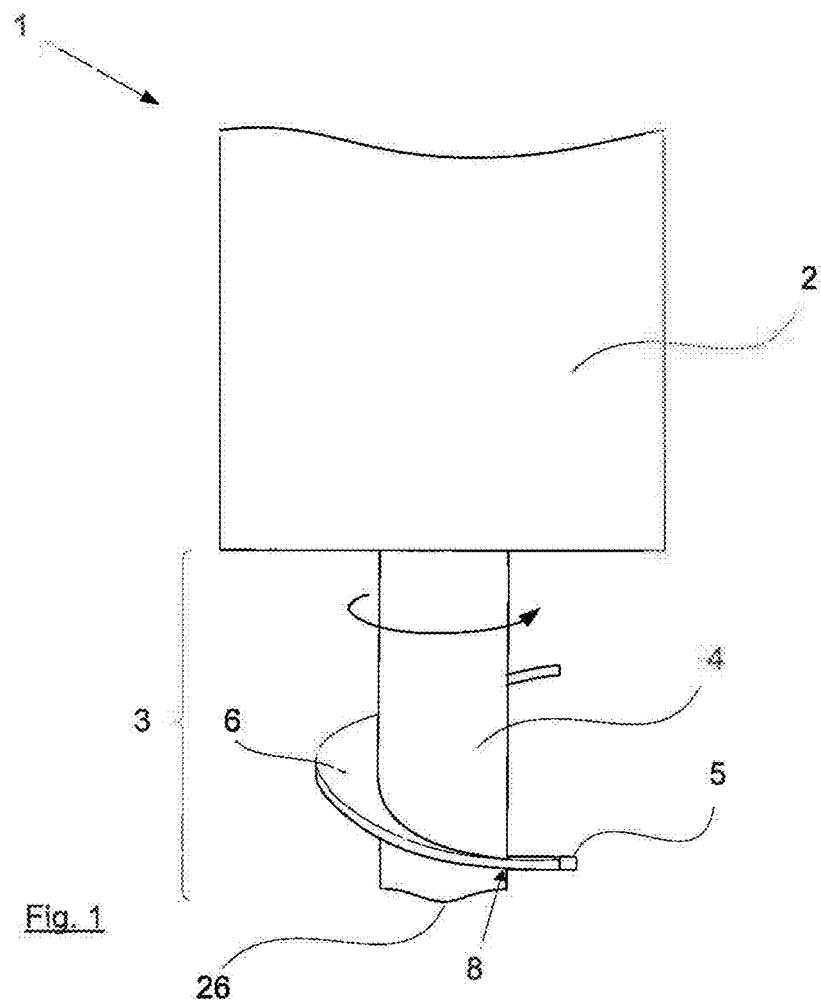
FIG. 1 is a schematic side view of a tool according to the invention for oral surgery.

FIG. 1 shows a tool 1 for oral surgery for cutting a helical groove in a mandible that is not shown here for the sake of simplicity. The tool 1 has a body 2 and a tool part 3. A drive shaft 9 extends at least partially into the body 2; see FIG. 3. The tool part 3 extends from the body. It comprises a rotatable shaft 4 that projects coaxially from the body 2. On its end opposite the body 2, the shaft 4 has an aperture 8 through which a pin 5 extends. The pin 5 is the actual tool and can be moved parallel to its longitudinal axis. It is connected to one end of a vibratory shaft 7 that extends in the shaft 4 and at whose other end vibrations are applied or produced that are transmitted along the vibratory shaft such that the pin oscillates longitudinally. According to a first variant, the surface of the pin 5 is diamond surfaced at least in the region projecting out of the shaft 4, so that it acts as a file as a result of the oscillating movement.

Figure 2:
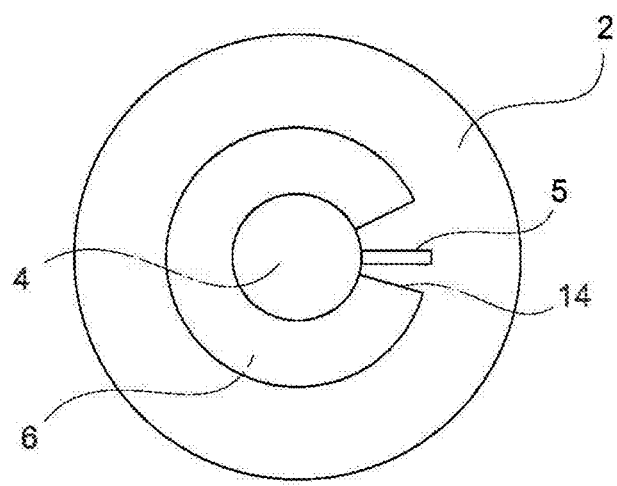
FIG. 2 is a schematic view from below of the tool for oral surgery.

A wing 6 projects radially from the outer surface of the shaft 4 and extends helically peripherally on the shaft 4. FIG. 2 shows a view from below of the tool 1 according to the invention for oral surgery. It is clear from this illustration that a leading edge 14 of the wing 6 is spaced rearward from the pin and extends helically upward beginning at the same level as the pin 5 with respect to the shaft axis along the outer periphery of the shaft 4, i.e. it winds in a helix around the shaft outer surface. In so doing, the wing 6 does not extend all the way around, but only through about 4/5 of a circle.

The wing 6 is not self-cutting. Its radially leading edge is blunt. A thickness D2 of the wing 6 (see FIG. 3) in the direction of a perpendicular to the wing 6 is about 1 mm. The pin 5 projects slightly farther out of the shaft 4 than the radial width of the wing 6 is, so that the wing 6 does not contact the bone wall of the groove.

The shaft 4 is rotatably coupled with the drive shaft 9 in order to transmit torque to the pin 5, i.e. advance angularly as shown by the arrow in FIG. 1. The rotation here is such that the pin 5 is forward in the direction of rotation and the wing 6 trails the pin 5 like a tail.

Figure 3:
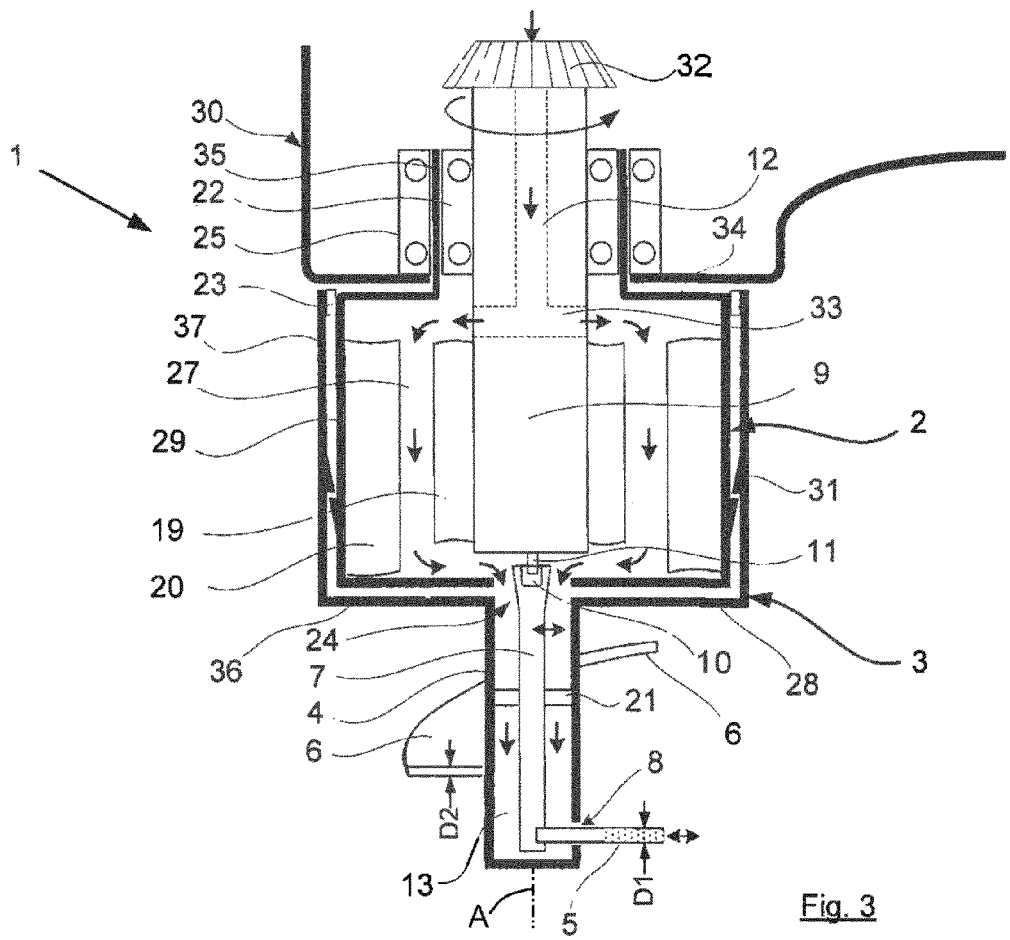
FIG. 3 is a schematic section through a tool according to the invention for oral surgery.

FIG. 3 shows a detailed illustration of an example of the tool 1 according to the invention in section. It should be noted that this is merely a schematic diagram intended to illustrate the functionality of the tool 1 according to the invention. Some technical details that ensure the functionality of the tool, such as retaining means or seals, for example, have been omitted from the figure for the clarity's sake. Furthermore, the actual design of the tool can differ from the view in FIG. 3 without deviating from the basic idea of the invention.

The tool 1 is held in an angle chuck 30 that is well known in dentistry and pivotally mounted. A first bearing 25, embodied here as a ball bearing for the sake of example, into which the body 2 is inserted acts as a support. A driven shaft (not shown) in the angle chuck 30 rotates a bevel gear 32 provided at the end of a drive shaft 9 of the tool 1. Rotation of the shaft in the angle chuck 30 is consequently transmitted by the bevel gear 32 to the drive shaft 9 of the tool 1.

In this embodiment, the body 2 of the tool 1 is drum-shaped. It has a tubular housing 29 closed at least partly at its ends by respective annular disks 34, 36. On the chuck side, a tubular collar 35 extends from the rear annular disk 34 coaxial to the housing 29 and fixed to the annular disk 34. The housing 29, the collar 35 and the two annular disks 34 and 36 can be made in one piece as a single component, from metal for example. Another bearing 22, here a ball bearing for example, in which the drive shaft 9 is supported is provided inside the collar 35. The collar 35 rests against the outside of the first bearing 25, and the body 2 is pivotal on the angle chuck 30.

Figure 4:
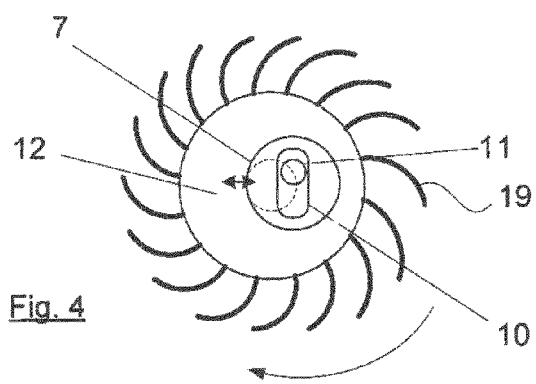
FIG. 4 is a schematic view of the coupling between vibratory shaft and eccentric pin.

The drive shaft 9 extends through the second bearing 22 into the housing 29. At the front end facing away from the angle chuck 30, the drive shaft 9 has on its outer periphery an array of radially projecting fins 19. They are angularly equispaced around the outer surface of the drive shaft 9 and extend outwardly and forward in the direction of rotation of the drive shaft 9 in an arc. This is illustrated by FIG. 4 that shows a view of the drive shaft 9 from below.

Another array of fins 20 extend radially inward from the inner surface the body housing 29 substantially in arcs, their arcs being opposed to those of the fins 19 of the drive shaft 9. The fins 19 of the drive shaft and the fins 20 of the body housing 29 are spaced apart from each other with a gap 27 between them that is filled by a fluid. This fluid can be a gas such as air, for example. When rotated, the fins 19 of the drive shaft 9 act as a fan impeller and generate a kind of cyclone of rotating air in the body housing 29. This exerts a compressive force on the concave sides of the fins 20 of the body housing 29 that results in torque about the axis of rotation of the body 2. A hydrodynamic coupling is thus formed between the drive shaft 9 and the body 2. By using a liquid—water, for example—this transmission of force is even stronger. The level of force transmission can be influenced not only by the type of fluid but also by the number and length of the fins 19 and 20.

The housing 29 of the body 2 is enclosed by the tool part 3. In the variant according to FIG. 3, the tool part 3 is also drum-shaped. It has a tubular housing 37 having a larger diameter than the housing 29 of the body 2 that completely encloses the body housing 29. The tool part 3 is a wear and can be replaced as needed. For this purpose, the tool part 3 is plugged detachably onto the body 2. The parts are joined coaxially with respect to each other, for example by a snap connection or bayonet joint. In FIG. 3, detents 31 can be seen that ensures an axial attachment of the tool part housing 37 to the body housing 29.

The tubular housing 37 of the tool part 3 is closed at the end facing away from the angle chuck 30 by a concentric annular disk 28 having a central hole 24. The tubular shaft 4 that is firmly connected to the annular disk 28 surrounds the hole 24 concentrically to the annular disk 28. Here as well, the housing 37, the annular disk 28 and the shaft 4 can be manufactured in one piece as a single component, for example from metal.

The vibratory shaft 7 in the shaft 4 is formed by a rod and extends coaxially in the shaft 4 until close to the lower shaft end. It is held by a fixed bearing ring 21. The pin 5 is attached to the front end of the vibratory shaft 7 remote from the body 2 and, in the embodiment according to FIG. 3, is diamond surfaced on the region projecting out of the shaft 4. The vibratory shaft 7 projects at its opposite rear end through the hole 24 in the annular disk 28 and through a corresponding opening in the annular disk 36 of the body 2 and into the body 2. It is coupled at this end to the drive shaft 9.

This coupling is effected by a slot 10 formed in the rear end of the vibratory shaft 7 into which an eccentric pin 11 carried on the drive shaft 9 projects. The eccentric pin 11 is slightly offset to the axis of rotation of the drive shaft, so that it moves a circular orbit when the drive shaft 9 rotates. This circular orbit path is shown by a broken line in FIG. 4.

FIG. 4 is a radial section through the end of the vibratory shaft at the level of the slot 10 and eccentric pin 11 seen from under the drive shaft 9. The eccentric pin 11 moves along its circular path back and forth within the slot 10. In doing so, it presses alternatingly against the longitudinal flanks of the slot 10 and entrains the vibratory shaft 7 along on its circular path, so that it oscillates transverse to the longitudinal extension of the slot 10. This movement is shown by the double arrow in FIG. 4. The drive shaft 9 can rotate at a speed between 20,000 rpm and 40,000 rpm. This results in an oscillation in the range between 50 kHz and 600 Hz. The amplitude of the oscillation can be established by the radial spacing of the eccentric pin 11 from the axis of rotation of the drive shaft 9.

The vibrations produced at the end propagate along the vibratory shaft 7 from the coupling to the opposite front end at which the pin 5 is located. Approximately in the middle between the eccentric pin 11 and the pin 5, the fixed bearing ring 21 is provided as a disk through which the vibratory shaft 7 extends concentrically. By means of this fixed bearing disk 21, against which the vibratory shaft 7 is supported, vibrations of the shaft 7 are suppressed at that location, and the vibratory shaft 7 is stabilized within the shaft 4. Nonetheless, vibrations rearward the fixed bearing ring 21 are transmitted, so that the pin 5 vibrates longitudinally along its longitudinal axis as indicated by the double arrow in FIG. 3. Due to the diamond surfacing, the pin 5 acts like a file and files away the bone material in the mandible.

According to an alternative to the fixed bearing disk 21 (not shown), the vibratory shaft 7 can be supported by a pivot in the shaft 4. This pivot can be implemented, for example, by having two opposing pins project that are held in respective seats in the shaft so as to be pivotably supported. Instead of these seats adapted in their shape and size to the pins, the shaft 4 can have a simple annular step on which the pins rest. Advantageously, a concentric sleeve is also pushed onto the shaft from the direction of the drive shaft and reaches in the axial direction to near the pins, so that it is on the side of the pins opposite this step and can additionally limit the vibratory shaft 7 in its freedom of motion. The two pins form an axis about which the vibratory shaft 7 pivots during oscillation.

The pin 5 has a thickness D1 that is greater than the thickness D2 of the wing 6. If the thickness D2 of the wing 6 is 1 mm, the thickness D1 of the pin 5 can be 1.2 mm, for example. The pin 5 can have a round or oval cross section; in the case of an oval cross section, the flat sides of the pin 5 are oriented in the angular direction of the shaft 4, i.e. in the direction of rotation of the shaft.

As already mentioned, the shaft 4 is rotatable. This is made possible by the fact that it is firmly connected to the housing 37 of the tool part 3 and the latter, in turn, is rotationally fixed on the housing 29 of the body 2. A rotationally fixed connection between the housings 29 and 37 of the body 2 and tool part 3 can be achieved, for example, by radial projections and/or recesses that form at least one stop, preferably several stops, with each other in the peripheral direction.

It is advantageous if liquid flows out of the shaft to rinse the groove produced by the pin 5. As a result of the rinsing, bone particles abraded by the pin 5 are washed out of the groove. The diamond surface of the pin 5 is also cleaned to maintain the file effect of the pin. To make this possible, liquid flows through the entire tool 1 according to the invention, which is indicated by corresponding arrows in FIG. 3. The liquid—sterilized water for example—is fed into the angle chuck 30. The drive shaft 9 is at least partly tubular and has an inner passage 12 that extends from the end of the drive shaft 9 on the chuck side into the body 2. The passage 12 is open at the end of the drive shaft 9, so that the liquid in the angle chuck 30 can enter there.

One or more transverse bores 33 are provided in the region within the body 2 that connect the passage 12 to the interior 27 of the body 2. The liquid can this pass through these transverse bores 33 out of and into the interior 27, where it acts as a torque transmission medium of the hydrodynamic coupling.

On the side of the body 2 opposite the angle chuck 30, the liquid flows through the central opening of the annular disk 36 and through the hole 24 of the other annular disk 28 of the tool part 3 and then enters the interior 13 of the shaft 4 where it flows parallel to the vibratory shaft 7. A seal 23 between the body housing 29 and the tool part housing 37 prevents liquid from coming out of the gap between body 2 and tool part 3.

To enable liquid to come out at the end of the shaft 4, the front end 6 can be uneven as shown in FIG. 1. According to this variant, it has two opposing projections that are formed by a shape of the front edge 26 that is approximately diametrally sinusoidal. The projections cause the front edge 26 of the shaft 4 not to rest over its entire surface against the bottom of the bore in the mandible. The projections thus maintain the region of the front edge 26 located between the projections spaced apart from the bottom of the bore so that liquid can come out of the shaft 4 under the front edge 26.

However, the front side of the shaft 4 can also be flat, as can be seen in FIG. 3. The liquid can then alternatively or additionally come out through the annular gap in the aperture 8 between the pin 5 and the shaft 4.

Figure 5:
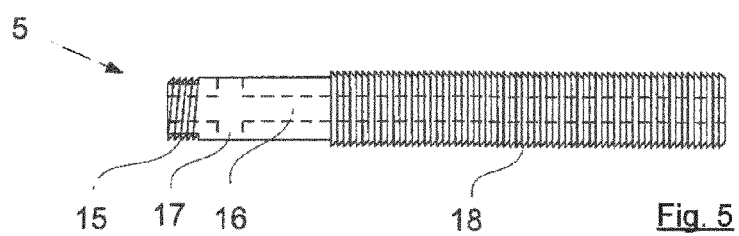
FIG. 5 is a view of a pin with saw-tooth profile.

As shown in FIG. 5, a provision is also made that a passage 16 extends longitudinally of the pin 5 that is open to both axial sides of the pin 5. The liquid can enter into this passage 16 through radially extending transverse bores 17. The liquid then flows out of the end of the pin 5 remote from the vibratory shaft 7 and, from there, through the entire groove produced.

As can also be seen from FIG. 5, the pin 5 has a screwthread 15 at its end at the vibratory shaft 7 with which it can be screwed into the shaft 7. This enables the pin 5 to be replaced if worn.

Moreover, FIG. 4 shows a surface of the pin 5 that is not diamond surfaced. According to this variant, its part projecting out of the shaft 4 has rotationally symmetrical saw teeth 18. As a result of these teeth 18, longitudinal oscillation of the pin 5 does not produce a filing effect but a sawing abrasion of bone material. This has the advantage that the helical groove can be formed substantially faster.

It should be noted that, in order to utilize the tool 1 according to the invention, a bore is required in the mandible whose interior diameter should correspond at least to the outer diameter of the shaft 4 so that the lower part of the shaft 4 can be inserted into this bore until the pin 5 comes into contact with the upper face of the mandible. The drive shaft 9 is then activated, so that the pin 5 starts oscillating longitudinally and abrades bone material. At the same time, torque is exerted by the drive shaft through the hydrodynamic coupling onto the tool part 3, the shaft 4 and the pin 5, so that the pin 5 works against the bone and, as the formation of the groove progresses, slowly performs a rotational movement. Superposition of these two movements works the pin 5 obliquely into the mandible.

As soon as the pin 5 has cut two to three millimeters into the mandible at a peripheral angle of about 90°, the wing 6 is already projecting into the groove formed in this way, the wing 6 extends farther into this groove as the groove is cut deeper, particularly in a nearly form-fitting manner. This stabilizes the tool 1 and prevents tilting, so that the axis of the helical groove is coaxial to the bore and can receive the implant body of a dental implant with its commensurately helical wing for anchoring the implant in a form-fitting manner.

In this way, only minimal bone material is removed from the mandible, the healing process, during which the mandible osseointegrates with the dental implant, is substantially shortened.

The invention claimed is:

1. A surgical tool for cutting a helical groove in a bone comprises a body receiving at least a portion of a drive shaft and a tool part held thereon comprising a functional element configured to produce the groove in the bone by performing an oscillating movement, the tool part comprising a projecting, rotatable shaft whose end opposite the body includes a first pin constituting the functional element extends through an aperture out of the rotatable shaft that, in order to remove material of the bone, can oscillate in its longitudinal direction, and that the rotatable shaft is coupled in such a way with the drive shaft that the drive shaft exerts torque on the rotatable shaft and the first pin at least indirectly, at least one wing projecting radially from the rotatable shaft extends at a spacing behind the first pin in the peripheral direction of the shaft helically in the direction of the body, wherein the rotatable shaft is coupled with the drive shaft by a hydrodynamic coupling.

2. The surgical tool defined in claim 1, wherein the first pin is diamond surfaced on its outside or has a saw tooth profile.

3. The surgical tool defined in claim 1, wherein the wing extends around ⅔ to ⅘ a periphery of the rotatable shaft.

4. The surgical tool defined in claim 1, wherein the wing has a radial width that is 0.5 to 1.2 times a diameter of the rotatable shaft.

5. The surgical tool defined in claim 1, wherein the drive shaft has an eccentric pin projecting from its front end that is in engagement with a vibratory shaft extending through the shaft, the eccentric pin being firmly held on the vibratory shaft.

6. The surgical tool defined in claim 5, wherein the vibratory shaft is supported on a fixed bearing disk that is approximately in the middle of the vibratory shaft.

7. The surgical tool defined in claim 1, further comprising a second pin diametrically opposite from the first pin, extends through another aperture out of the shaft that alternately to the first pin, can oscillate in order to exert a file effect longitudinally.

8. The surgical tool defined in claim 7, a second wing projects radially from the rotatable shaft and extends at a spacing beginning behind the second pin angularly of the shaft helically toward the body.

9. The surgical tool defined in claim 1, wherein an opening is provided in the rotatable shaft next to the first pin on the side opposite the wing on the same radial plane as the first pin.

10. A tool for cutting a helical groove in a bore in a bone, the tool comprising:
a drive housing;
a drive shaft rotatable in the drive housing;
a fluid coupling between the drive shaft and the drive housing;
a tube fixed on the housing, extending along an axis from the housing, and fittable into the bore;
a helically extending guide wing centered on the axis, projecting radially from the tube and having a leading end relative to a direction of rotation of the housing and tube by the fluid coupling;
a vibratory shaft inside the tube and having a rear end in the drive housing and an opposite front end;
a machining pin projecting radially from the front end of the vibratory shaft through the tube at an angular spacing forward of the leading end of the guide wing; and
a drive in the housing and connected to the rear end of the vibratory shaft for radially oscillating the pin.

\* \* \* \* \*